(12) United States Patent
Ngo et al.

(10) Patent No.: US 6,790,413 B2
(45) Date of Patent: Sep. 14, 2004

(54) SAMPLE PRESENTATION UNIT (75) Inventors: Dang M. Ngo, Fountain Valley, CA (US); Brian D. Wilson, Chaska, MN (US); Robert J. Mattila, Jordan, MN (US)

(73) Assignee: Beckman Coulter, Inc., Fullerton, CA (US)

( * ) Notice: Subject to any disclaimer, the term of this patent is extended or adjusted under 35 U.S.C. 154(b) by 538 days.

(21) Appl. No.: 09/848,450

(22) Filed: May 3, 2001

(65) Prior Publication Data

US 2002/0164269 A1 Nov. 7, 2002

(51) Int. Cl.⁷ ................................. B32B 5/02
(52) U.S. Cl. ..................... 422/65; 422/63; 422/66; 422/67; 422/100
(58) Field of Search .................. 422/63, 65, 66, 422/67, 100

(56) References Cited

U.S. PATENT DOCUMENTS

| | | | |
|---|---|---|---|
| 2,967,633 A | 1/1961 | Stegemann et al. | |
| 3,724,638 A | 4/1973 | Peters et al. | 198/24 |
| 4,582,990 A | 4/1986 | Stevens | 250/328 |
| 4,798,703 A | 1/1989 | Minekane | 422/65 |
| 4,861,554 A | 8/1989 | Sakuma | 422/65 |
| 4,898,271 A | 2/1990 | Schiessl | 198/444 |
| 5,207,331 A | 5/1993 | Teegarden et al. | 209/556 |
| 5,209,903 A * | 5/1993 | Kanamori et al. | 422/65 |
| 5,306,510 A | 4/1994 | Meltzer | 422/65 |
| 5,380,488 A * | 1/1995 | Wakatake | 422/65 |
| 5,411,065 A | 5/1995 | Meador et al. | 141/1 |
| 5,428,470 A | 6/1995 | Labriola, II | 359/119 |
| 5,439,645 A | 8/1995 | Saralegui et al. | 422/64 |
| 5,443,791 A | 8/1995 | Cathcart et al. | 422/65 |
| 5,538,849 A * | 7/1996 | Uematsu et al. | 435/6 |
| 5,735,387 A | 4/1998 | Polaniec et al. | 198/690.1 |
| 5,833,925 A * | 11/1998 | Shu et al. | 422/63 |
| 5,853,667 A * | 12/1998 | Seaton et al. | 422/65 |

(List continued on next page.)

FOREIGN PATENT DOCUMENTS

| | | | |
|---|---|---|---|
| EP | 0866335 | 9/1998 | G01N/35/04 |
| JP | 08035970 | 2/1996 | G01N/35/04 |

*Primary Examiner*—Jan Ludlow
*Assistant Examiner*—Brian R Gordon
(74) *Attorney, Agent, or Firm*—William H. May; D. David Hill; Hogan & Hartson, LLP (57) ABSTRACT

A sample presentation unit (SPU) for an automated analyzer is provided. The SPU has a sample rack onload section having an elongated rail, and an onload moving mechanism movable along the rail for moving the sample racks placed on the rail towards a sample rack presentation section. The sample rack presentation section of the SPU has a transfer area connected to the proximal end of the rail of the sample rack onload section for receiving the sample racks from the sample rack onload section, a sample presentation area adjacent to the automated analyzer for presenting sample racks for aspiration, and a presentation moving mechanism movable between the transfer area and the presentation area for moving sample racks from the transfer area to the presentation area for a sample aspiration and subsequently moving the sample racks from the presentation area back to the transfer area after sample aspiration. The SPU also has a sample rack offload section having an offload area connected to the transfer area of the sample rack presentation section for receiving the sample racks from the sample rack presentation section after sample aspiration, and an offload moving mechanism for moving the sample racks received from the sample rack presentation section to a sample rack offload tray. The SPU further has a plurality of strategically located sensors for detection of motion errors or motor jams.

47 Claims, 6 Drawing Sheets

U.S. PATENT DOCUMENTS

| | | | |
|---|---|---|---|
| 5,876,670 A | | 3/1999 | Mitsumaki et al. ............ 422/65 |
| 5,902,549 A | * | 5/1999 | Mimura et al. ................ 422/65 |
| 5,972,295 A | | 10/1999 | Hanawa et al. ................ 422/65 |
| 5,985,215 A | * | 11/1999 | Sakazume et al. ............ 422/67 |
| 6,019,945 A | * | 2/2000 | Ohishi et al. ................. 422/65 |
| 6,040,192 A | | 3/2000 | Tuunanen ................... 436/177 |
| 6,080,364 A | * | 6/2000 | Mimura et al. ................ 422/67 |
| 6,117,392 A | * | 9/2000 | Hanawa et al. ................ 422/65 |
| 6,220,451 B1 | * | 4/2001 | Hoffmann ................... 209/522 |
| 6,261,521 B1 | * | 7/2001 | Mimura et al. ................ 422/67 |
| 6,426,044 B1 | * | 7/2002 | Cohen et al. ................. 422/63 |
| 6,440,368 B1 | * | 8/2002 | Cohen et al. ................. 422/63 |
| 6,444,171 B1 | * | 9/2002 | Sakazume et al. ............ 422/65 |
| 6,451,259 B1 | * | 9/2002 | Cohen et al. ................. 422/63 |
| 6,455,002 B1 | * | 9/2002 | Jokes et al. ................... 422/63 |
| 6,458,324 B1 | * | 10/2002 | Schinzel ...................... 422/65 |
| 6,521,183 B1 | * | 2/2003 | Burri et al. ................... 422/65 |
| 6,522,976 B2 | * | 2/2003 | Shiba et al. .................. 702/22 |
| 6,599,749 B1 | * | 7/2003 | Kodama et al. .............. 436/47 |
| 2002/0021983 A1 | * | 2/2002 | Comte et al. ................. 422/65 |
| 2003/0021728 A1 | * | 1/2003 | Sharpe et al. ................. 422/67 |
| 2003/0049171 A1 | * | 3/2003 | Tamura et al. ................ 422/64 |

* cited by examiner

SAMPLE PRESENTATION UNIT

BACKGROUND OF THE INVENTION

1. Area of the Art

The invention relates generally to sample handling mechanisms for automated chemical analyzers, and specifically to a sample presentation unit for automated immunodiagnostic instruments.

2. Description of the Prior Art

Automated chemical analyzers and automated immunodiagnostic instruments are widely used in clinical chemistry sampling and analyzing applications, and often involve the presentation of samples for performing various assays. Many automated analyzers and immunodiagnostic instruments require automated loading systems for sample presentation. Therefore, some of the requirements of the sample loading system are that the system has a common appearance and functionalities, and is adaptable or easily modifiable to adapt to various immunodiagnostic instruments.

Another requirement of an automated sample loading system is that the system must be able to quickly detect a motor jam during operation to avoid mistakes or damages to the samples.

In addition, it is a requirement of an automated sample loading system to read sample identifications often presented in bar code labels ahead of time to allow information to be downloaded from the common host computer that controls the operation of the immunodiagnostic instrument.

While many mechanisms have been developed for handling samples, they all have certain limitations and therefore cannot satisfy all of the requirements and needs addressed by the present invention. Therefore, it is desirable to provide a new system for presenting samples for processing and analyzing by the immunodiagnostic instruments.

SUMMARY OF THE INVENTION

It is an object of the present invention to provide a system for presenting samples to automated chemical analyzers.

The objects and advantages of the present invention are achieved in a sample presentation unit by having a sample rack onload section, a sample rack presentation section, and a sample rack offload section all connected as one unit.

The sample rack onload section has an elongated rail having a distal end and a proximal end, an onload pusher driven by an onload motor and movable along the rail for moving the sample racks placed on the rail towards the proximal end of the rail, and an onload sensor located adjacent to the proximal end of the rail of the sample rack onload section for detection of motion errors or jams of the onload moving mechanism.

The sample rack presentation section has a transfer area connected to the proximal end of the rail of the sample rack onload section for receiving the sample racks from the sample rack onload section, a sample presentation area adjacent to the automated analyzer for presenting sample racks for aspiration, an alignment mechanism for precise positioning of sample tubes, a presentation tray driven by a presentation motor and movable between the transfer area and the presentation area for simultaneously moving a multiplicity of the sample racks from the transfer area to the presentation area for sample aspiration and subsequently moving the multiplicity of the sample racks from the presentation area back to the transfer area after sample aspiration, and a presentation sensor located at the presentation area of the sample rack presentation section for the detection of motion errors or jams of the presentation moving mechanism.

The sample rack offload section has an offload area connected to the transfer area of the sample rack presentation section for receiving the sample racks from the sample rack presentation section after sample aspiration, an offload pusher driven by an offload motor for moving the sample racks received from the sample rack presentation section to a sample rack offload tray, and an offload sensor located at the offload queue area of the sample rack offload section for the detection of motion errors or jams of the offload moving mechanism.

The sample presentation unit of the present invention may also have a bar code reader located adjacent to the transfer area of the sample rack presentation section for obtaining the identification of the sample racks prior to presenting the sample racks to the automated analyzer for aspiration.

Such an arrangement has been found to provide a number of advantages. As explained in greater detail below, the sample presentation unit of the present invention is a modular system that can be moved away to provide access to other components of the automated analyzer. Since the entire system can be moved together, all alignment information will stay intact.

The modular system design of the sample presentation unit of the present invention also provides a common appearance and functionalities, and is adaptable or easily modifiable to adapt to various automated chemical or immunodiagnostic analyzers.

In addition, the sample presentation unit of the present invention employs strategically located sensors for the quick detection of a motor jam during operation to avoid mistakes or damages to the samples.

Furthermore, the sample presentation unit of the present invention is capable of reading sample identifications ahead of time to allow information to be downloaded from the main host computer that controls the operation of the immunodiagnostic instrument.

The sample presentation unit of the present invention may be used in connection with any automated chemical or immunodiagnostic analyzers that require sample presentations. Examples of such analyzers include, but are not limited to, Access® Special Chemistry Analyzer (Beckman Coulter Inc., CA), and SYNCHRON LX®20 General Chemistry Analyzer (Beckman Coulter Inc., CA), and the like.

The invention is defined in its fullest scope in the appended claims and is described below in its preferred embodiments.

DESCRIPTION OF THE FIGURES

The above-mentioned and other features of this invention and the manner of obtaining them will become more apparent, and will be best understood by reference to the following description, taken in conjunction with the accompanying drawings. These drawings depict only a typical embodiment of the invention and do not therefore limit its scope. The drawings serve to add specificity and detail, in which.

DETAILED DESCRIPTION OF THE INVENTION

The present invention is directed to a new sample presentation unit (SPU) used in conjunction with an automated chemical or immunodiagnostic analyzer.

The SPU of the present invention is used to transport the entire required test samples to and from a main sample aliquoting station of an automated analyzer. The SPU accepts samples in racks that have the capacity for up to, for example, four (4) tubes or sample cups. The racks are identified with user-oriented bar codes. The racks can be loaded on the SPU, either individually or in groups. Following the sample aspiration, the racks can be unloaded singly or as a group.

In general, the sample presentation unit of the present invention has a sample rack onload section, a sample rack presentation section, and a sample rack offload section, all connected as one unit.

The sample rack onload section of the present invention has an onload queue area, and an onload moving mechanism for moving the sample racks placed on the onload queue area to the sample rack presentation section.

The sample rack presentation section of the present invention has a transfer area connected to the onload queue area of the sample rack onload section for receiving the sample racks from the sample rack onload section, a sample presentation area adjacent to the automated analyzer for presenting sample racks for aspiration, a presentation moving mechanism movable between the transfer area and the presentation area for simultaneously moving a multiplicity of the sample racks from the transfer area to the presentation area for sample aspiration and subsequently moving the multiplicity of the sample racks from the presentation area back to the transfer area after sample aspiration, and an alignment mechanism to provide precise sample tube positioning during aspiration.

The sample rack offload section of the present invention has an offload section connected to the transfer area of the sample rack presentation section for receiving the sample racks from the sample rack presentation section after a sample aspiration, and an offload moving mechanism for moving the sample racks received from the sample rack presentation section to a sample rack offload tray.

Offload mechanism adds additional offload capacity by allowing the racks to "wrap" around the instrument. There are racks in the offload section on both sides of the offload moving mechanism.

The sample presentation unit of the present invention is provided with a bar code reader(s) for ascertaining sample rack identifications prior to presenting the sample racks for aspiration.

Having thus provided an overview of a certain embodiment of the present invention, this specification now provides a more detailed discussion of the preferred embodiments of the present invention with particular reference to the drawings.

Referring to FIGS. 1 through 4, there is shown an SPU 10 of the present invention that may be used in connection with an automated chemical analyzer, such as Access® Special Chemistry Analyzer, described above. The SPU 10 includes three (3) main interconnected modules or sections: an onload section 12, a presentation section 14, and an offload section 16.

The onload section 12 of the SPU 10 has an elongated rail 18 with a distal end 20 and a proximal end 22, an onload motor 24, an onload pusher 26, and an onload sensor 28 located near the proximal end 22 of the rail 18.

Figure 5:
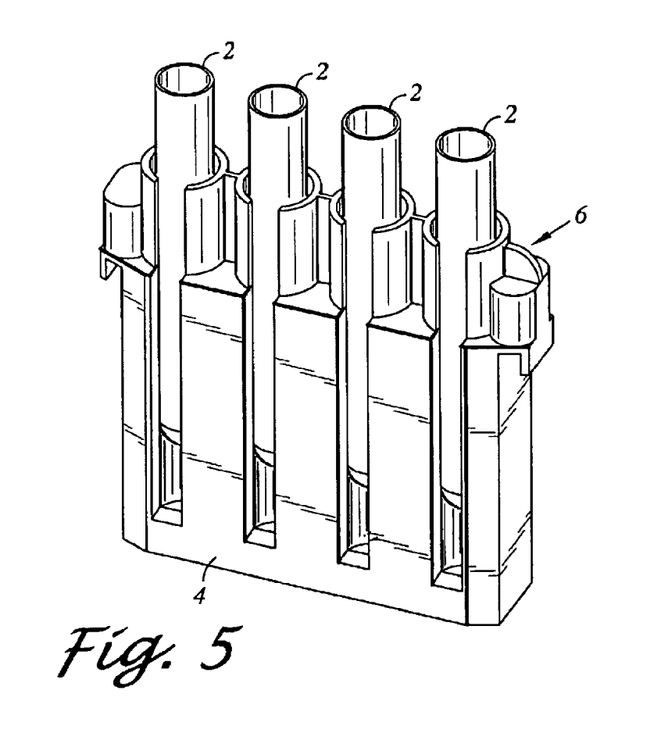
FIG. 5 is an illustrative perspective view of a sample rack used with the sample presentation unit of the present invention, showing the engagement feature of the sample rack.

When the cycle begins, the onload pusher 26 is moved by the onload motor 24 back to its "home" position near the distal end 20 of the rail 18. Sample racks 4 having an engagement feature 6 and holding multiple (typically 4) sample tubes 2 (as shown in FIG. 5) may be placed anywhere on the onload rail 18 as long as there is room available. Priority samples may be placed close to the -proximal end 22 of the rail 18. These racks consist of the "onload queue" 30.

Once the onload queue 30 is ready, the onload pusher 26 is moved by the onload motor 24 along the rail 18 to push the entire onload queue 30 towards the proximal end 22 of the rail 18 to the presentation section 14 of the SPU 10. During a run, this will also push any racks in a transfer area of the presentation section 14, as well as any racks in an offload staging area of the offload section 16 to an offload queue area of the offload section 16.

As the onload queue 30 is pushed towards the presentation section 14, the onload sensor 28 looks for the leading edge of a rack to determine if there are more sample racks to be run. If a rack is detected, it will then look for the trailing edge of the rack. Once the trailing edge is detected, the onload pusher 26 will continue moving another fixed distance to bring this rack to a transfer area of the presentation section 14.

The presentation section 14 of the SPU 10 has the transfer area 32, an aspiration area 34, a presentation motor 36, a presentation tray 38, a bar code reader (BCR) 40 located near the transfer area 32, and a presentation sensor 42 located at the remote end of the aspiration area 34.

Figure 6:
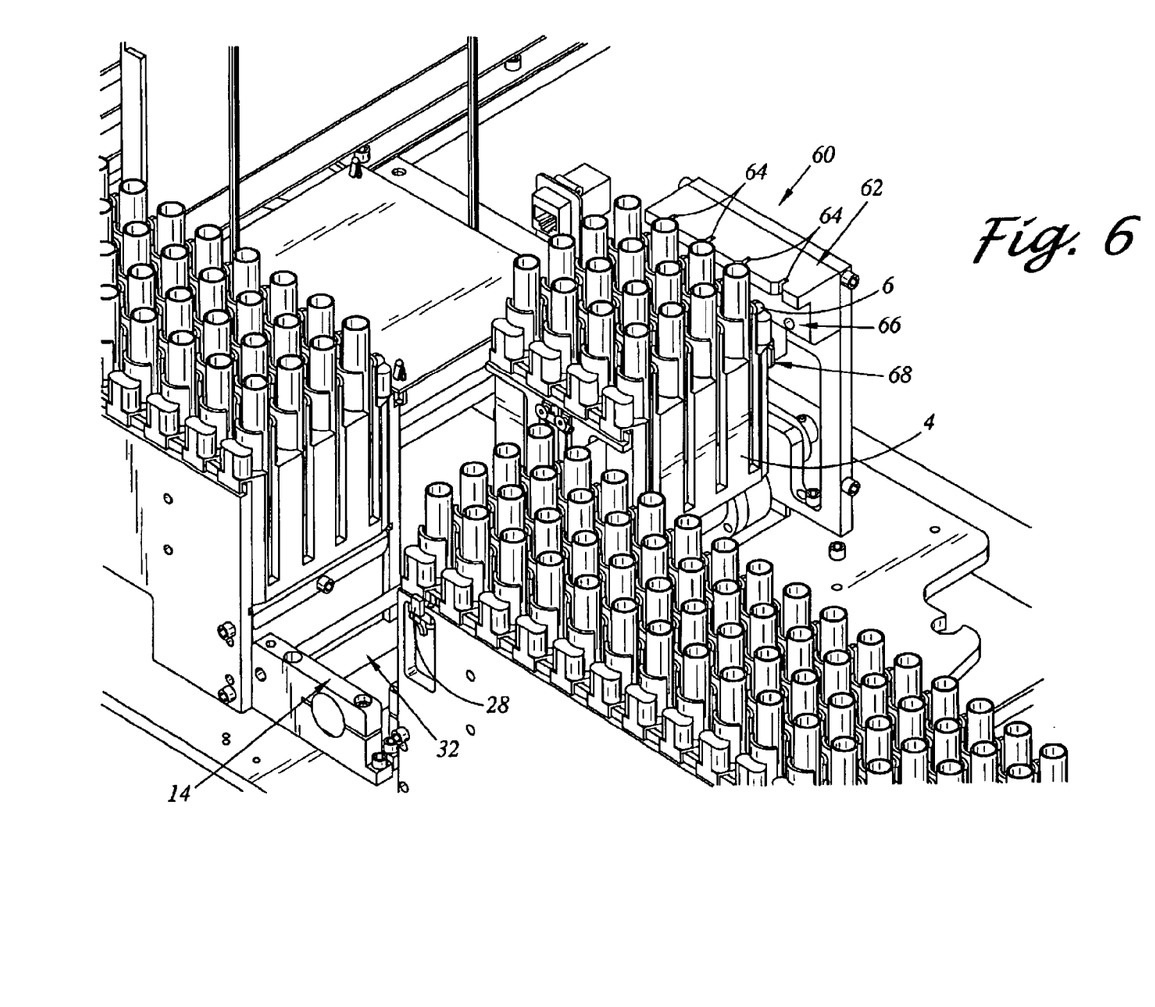
FIG. 6 is an illustrative perspective view showing the alignment mechanism of the sample presentation unit of the present invention.
Figure 7:
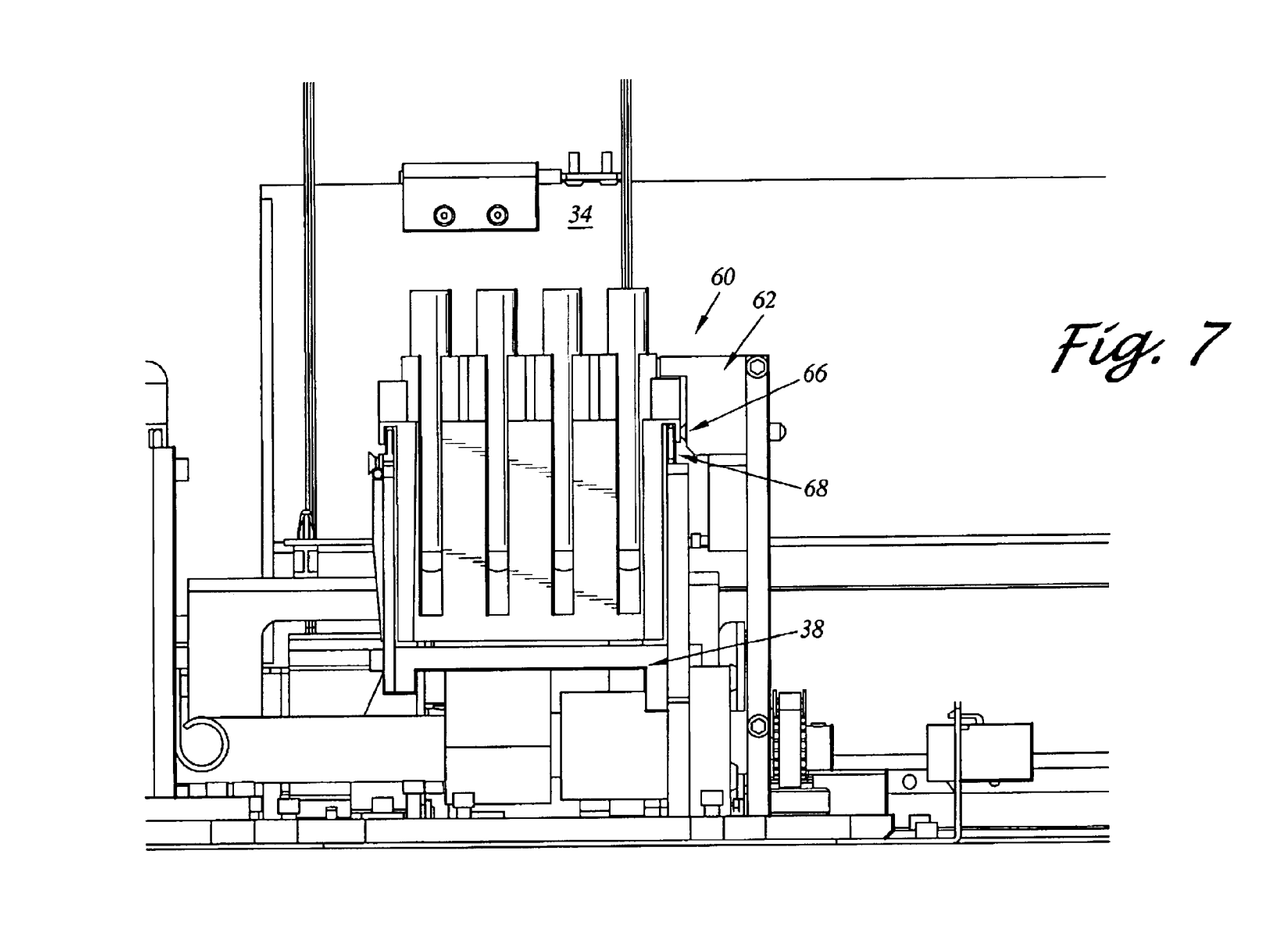
FIG. 7 is an illustrative side elevation view showing the alignment mechanism of the sample presentation unit of the present invention.

Variations in a sample tube position during aspiration from a sample tube 2 with a spherical- or conical-shaped bottom often prevent the sample probe from reaching its full depth inside the sample tube 2, resulting in increased dead volume or wasted sample. To ensure the precise positioning of the sample tube during aspiration, the present invention sample presentation unit 10 utilizes an alignment mechanism 60 to provide repeatable rack positions, which in turn provides precise sample tube positioning. Referring to FIGS. 5 through 7, the alignment mechanism 60 includes an alignment block 62 with precision machined "lead-in" slots 64 which can engage with the engagement feature 6 of the sample racks 4, and spring-biased plungers 66 which force the sample racks 4 against an alignment rail 68. At the same time the sample racks 4 are forced against the alignment rail 68, the "lead-in" feature 64 of the alignment block 62 forces the sample racks 4 to transport along the rail 68 into their final aspiration positions. By controlling the position and squareness of the sample racks 4, the precise positioning of all sample tubes 2 in the sample racks 4 are achieved. In addition, the distance between the lead-in slots 64 on the alignment block 62 is designed slightly wider than the width of each sample rack 4, such that when all sample racks 4 are engaged with the alignment block 62, they are slightly separated to make sure that they do not touch and interfere with each other during aspiration.

Figures 1, 2:
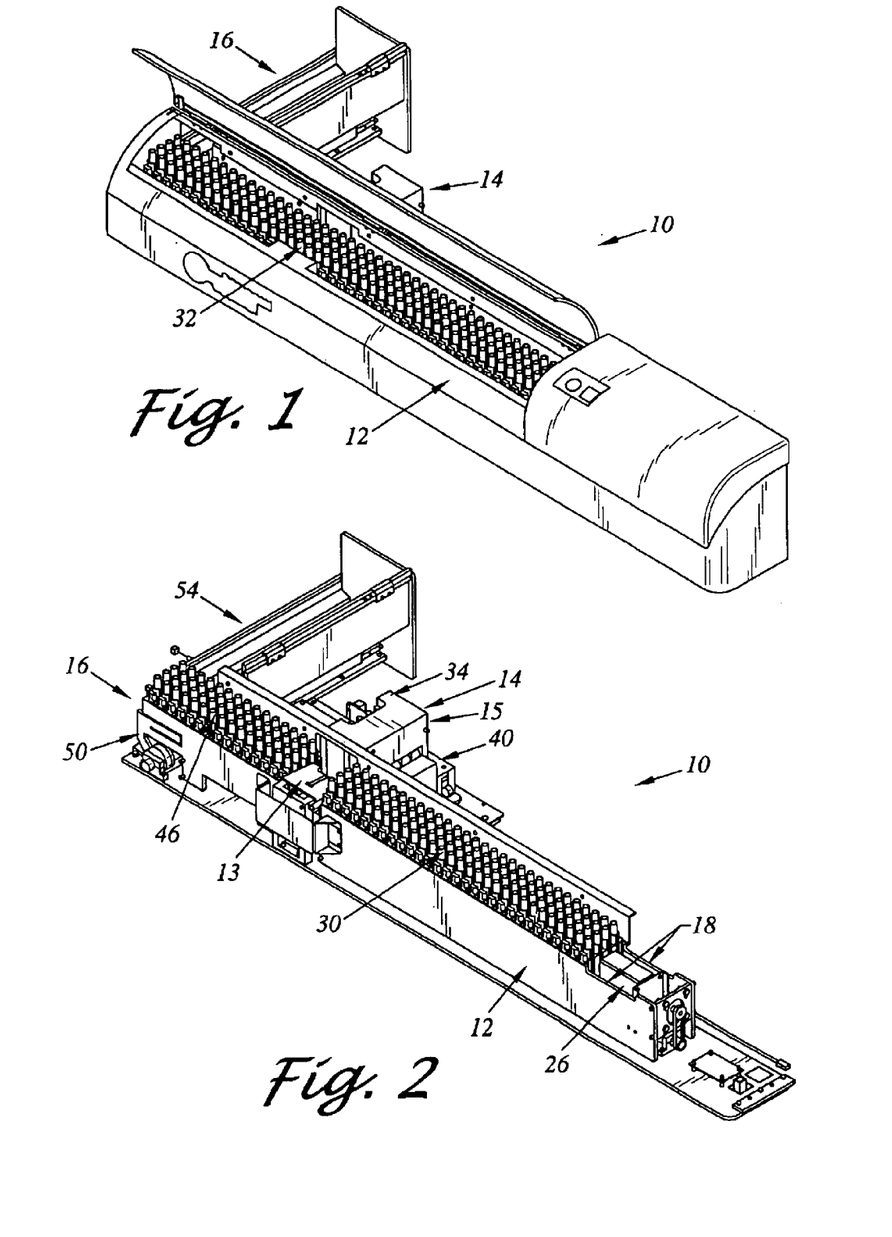
FIG. 1 is an illustrative perspective view of a preferred embodiment of the sample presentation unit of the present invention (with the modular unit cover shown), showing sample tubes loaded for presentation.
FIG. 2 is an illustrative perspective view of a preferred embodiment of the sample presentation unit of the present invention (with the modular unit cover and front panel removed to show the internal structure), showing sample tubes loaded for presentation for aspiration.
Figure 3:
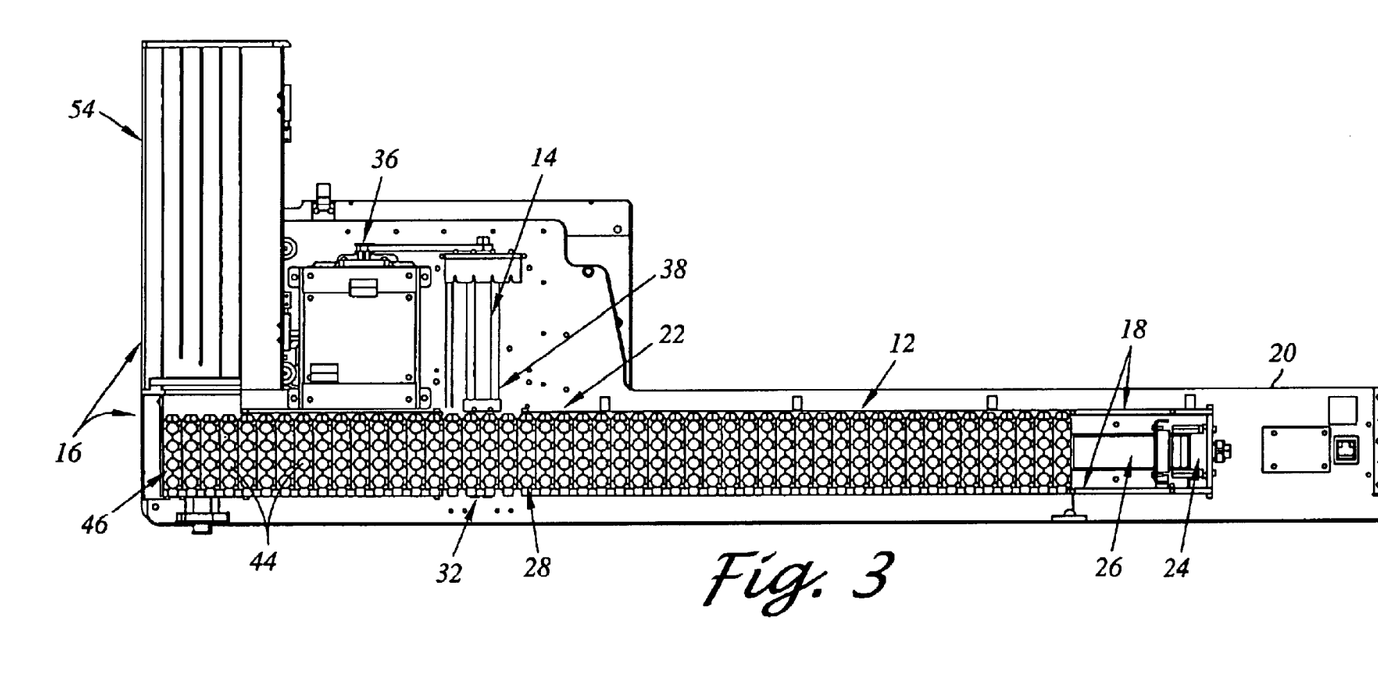
FIG. 3 is an illustrative top view of a preferred embodiment of the sample presentation unit of the present invention, showing sample tubes loaded for presentation.
Figure 4:
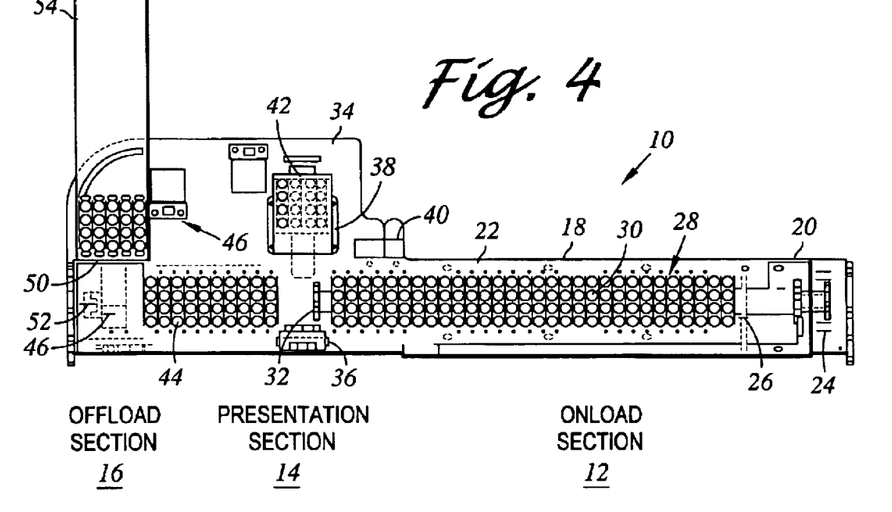
FIG. 4 is an illustrative perspective view of a preferred embodiment of the sample presentation unit of the present invention, showing sample tubes loaded for presentation for aspiration.

When the cycle begins, the presentation tray 38 is moved by the presentation motor 36 back to its "home" position at the transfer area 32, which also pushes a gate 13 (as shown in FIG. 2) of the presentation section 14 out of the way. After the leading racks of the onload queue 30 are pushed into the transfer area 32, the presentation tray 38 is moved forward by the presentation motor 36 to present these sample racks to the aspirate position for sample aliquoting by the main sample aliquoting station of the chemistry analyzer. BCR 40 reads the bar code label of the racks. The sample racks are properly aligned by the alignment mechanism 60, as described in detail above.

The presentation sensor 42 is provided to detect the status of the presentation motor 36. If the presentation motor 36 functions normally, then the presentation sensor 42 will be interrupted within a predetermined range before the presented racks get to the aspirate area 34; otherwise, there is a motion error or motor jam.

The offload section 16 of the SPU 10 has the offload staging area 44, an offload queue area 46, an offload motor 48, an offload pusher 50, an offload sensor 52 located near the offload queue area 46, and an offload tray 54.

The present invention SPU 10 may have two (2) distinct offload areas. One of these areas may be simply an extension of the onload and presentation rails. The other area may be perpendicular to the onload and presentation rails. This creates an additional challenge to the stability of the racks. While on the onload rails, the racks are suspended by features well above the center of gravity of the racks, making it impossible for them to fall or tip. When the racks are moved perpendicular to the onload and presentation rail, they are no longer suspended but rather sit on the bottom of the racks. This creates the problem of rack stability as they are being advanced by the offload pusher or during rack removal by the operator. To solve this problem, a series of thin protruding fins are provided extending up from the offload surface. These fins are adequately tall and spaced apart such that when a rack is placed between the fins, the rack is stabilized and cannot be tipped. When transitioning into the fins, adequate lead-in is provided on the racks and fins to compensate for slight errors in rack position.

When the cycle begins, the offload pusher 50 is moved by the offload motor 48 back to its "home" position at the offload queue area 46. The offload sensor 52 is used to determine whether the offload queue area 46 is full. If the offload queue area 46 is full, then the offload motor 48 will move the offload pusher 50 forward to push, for example, four (4) racks in the offload queue area 46 into the offload tray 54. The offload motor 48 will then move the offload pusher 50 back to its home position. However, before the offload pusher 50 gets back to its home position, the offload sensor 52 must be interrupted within a predetermined range; otherwise, it is an indication of a motion error or motor jam.

The SPU 10 is capable of allowing routine sample racks to be added during a run. When routine sample racks need to be added during a run, the onload pusher 26 will be moved by the onload motor 24 back to its home position. The operators can then add sample racks anywhere on the onload rail 18 as long as there is room available. "Priority" or "semi-priority" sample racks may be placed in front of the onload queue 30. During routine loading, the operator is locked out of the presentation section by the gate 13 and an enclosed aspiration area 15 (as shown in FIG. 2). The instrument can continue all operations with the presentation section during routine loading.

The SPU 10 is also capable of allowing very high priority sample racks to be added during a run. When high priority sample racks need to be added during a run, the operator initiates this loading operation by pressing a switch, then the onload pusher 26 is moved by the onload motor 24 back to its home position, and the presentation tray 38 is also moved by the presentation motor 36 back to its loading position. Then the operator can manually push any sample racks in the presentation tray 42 out of the transfer area 32 of the presentation section 14 and any racks on the rail 18 of the onload section 12 all the way towards the distal end 20 of the onload rail 18. The operator can then place STAT sample racks in front of the onload queue. If there is not enough room, the operator can remove some routine sample racks from the onload rail 18 to make room.

The sample presentation unit of the present invention is provided with the necessary electrical and electronic means for power supply, micro-processor control, and connection with the automated analyzer's main control system for integrated control and operation, all of which are evident to one skilled in the art in view of the instant disclosure.

The sample presentation unit of the present invention has many unique and advantageous features, including the modular system design that provides a common appearance and functionalities, and is adaptable or easily modifiable to adapt to various immunodiagnostic instruments, and that can be moved away to provide access to other components of the immunodiagnostic instrument while maintaining all alignment information.

Figure 8:
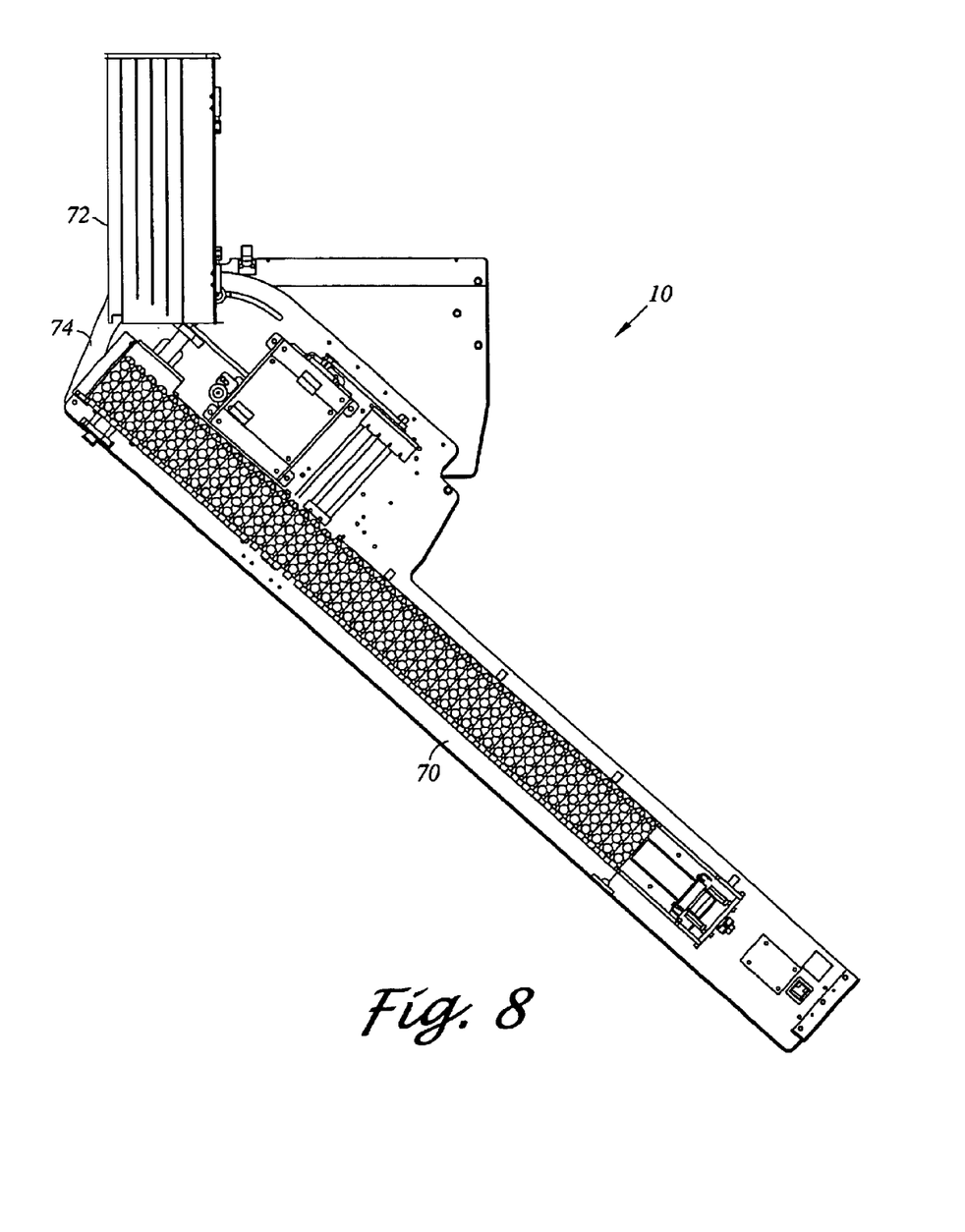
FIG. 8 is an illustrative top view of a preferred embodiment of the sample presentation unit of the present invention, showing the sample presentation unit of the present invention may have an offload area that is split into two linked areas.

In order to obtain adequate onload and offload rack capacity on an SPU, the SPU can become quite lengthy. One way to accommodate this is to combine the two offload query areas described above and effectively wrap the SPU module around the analyzer. This creates an additional problem because in many applications, the SPU would be in the front of an analyzer and therefore block service and maintenance access to the rest of the analyzer. To solve this problem, the present invention SPU 10 may be broken between the two offload areas, as shown in FIG. 8. The primary portion 70 of the SPU 10 containing the onload section, the presentation section, and the "in-line" offload area can be swung or rotated out away from the analyzer. In order to swing out the primary portion 70, the perpendicular offload area 72 is first transported out of the way. These motion areas are accomplished by adding a linkage connection 74 connecting the primary portion 70 and the perpendicular offload area 72 of the SPU 10. When the primary portion 70 is swung open, the linkage connection 74 drives the perpendicular offload area 72 ahead of it. When the primary portion 70 is swung back, the linkage connection 74 tightly connects the two portions together.

In addition, the sample presentation unit of the present invention is capable of the quick detection of motion errors or motor jams during operation through the use of strategically located sensors, and is also capable of ascertaining sample identifications ahead of time to allow information to be downloaded from the main host computer that controls the operation of the immunodiagnostic instrument. Automated analyzers can request test information from a host computer system to avoid manual station entry if data. Host computers may have a time lag of several minutes from being supplied a sample identification to its reply containing test request information. This test request information is necessary to determine what to do with a sample at the time of aspiration. To overcome this time lag, which could seriously diminish total test throughput, the SPU 10 is capable of moving multiple (for example, four) sample racks into the aspiration area 34. When a subject rack is initially brought into the aspiration area 34, it passes the bar code reader 40 and the query for the required tested information is sent to the host computer. Meanwhile, the aspiration processes for the three racks ahead of the subject rack are running, and by the time the subject rack is up for aspiration, the test request information for the subject tray from the host computer is returned. Using this technique, sample identifications are read well in advance of the actual aspiration. Since during a routine loading operation the aspiration area is protected from operator intervention, the sample order integrity is maintained.

The foregoing is meant to illustrate, but not to limit, the scope of the invention. Indeed, those of ordinary skill in the art can readily envision and produce further embodiments, based on the teachings herein, without undue experimentation. Suitable materials are commercially available and would be known to those of ordinary skill in the art in view of this disclosure.

It is to be understood that the form of the device depicted in the figures has been chosen only for the purpose of describing a particular embodiment and function of the invention, and that the material of the invention can be addressed in various ways and incorporated in other types of devices, all of which will be evident to those working in the art.

The present invention may be embodied in other specific forms without departing from its essential characteristics. The described embodiment is to be considered in all respects only as illustrative and not as restrictive. The scope of the invention is, therefore, indicated by the appended claims rather than by the foregoing description. All changes which come within the meaning and range of the equivalence of the claims are to be embraced within their scope.

What is claimed is:

1. An apparatus for presenting sample racks to an automated analyzer, comprising:
   a. a sample rack onload section, a sample rack presentation section, and a sample rack offload section;
   b. said sample rack onload section having an onload queue area, and an onload moving mechanism for moving said sample racks placed on said onload queue area to said sample rack presentation section;
   c. said sample rack presentation section having a transfer area connected to said onload queue area of said sample rack onload section for receiving said sample racks from said sample rack onload section, a sample presentation area adjacent to said automated analyzer for presenting sample racks for aspiration, and a presentation moving mechanism, movable between said transfer area and said presentation area for moving at least one of said sample racks from said transfer area to said presentation area for a sample aspiration and subsequently moving said at least one of said sample racks from said presentation area back to said transfer area after a sample aspiration, wherein said transfer area can hold a plurality of said sample racks wherein said plurality of sample racks can be presented simultaneously in said presentation area; and
   d. said sample rack offload section having an offload area connected to said transfer area of said sample rack presentation section for receiving said sample racks from said sample rack presentation section after a sample aspiration, and an offload moving mechanism for moving said sample racks received from said sample rack presentation section to a sample rack offload tray.

2. The apparatus as defined in claim 1, wherein said onload moving mechanism of said sample racks onload section comprises an onload pusher driven by an onload motor and capable of pushing either an individual one or a group of said sample racks.

3. The apparatus as defined in claim 1, further comprising an onload sensor for detection of motion errors or jams of said onload moving mechanism.

4. The apparatus as defined in claim 1, wherein said presentation moving mechanism of said sample racks presentation section further comprises means for simultaneously moving a multiplicity of said sample racks.

5. The apparatus as defined in claim 4, wherein said simultaneous moving means comprises a presentation tray driven by a presentation motor and capable of holding said multiplicity of said sample racks.

6. The apparatus as defined in claim 1, further comprising a bar code reader for obtaining identification of said sample racks, or of one or more sample containers held by said sample racks, or of sample contents contained in said containers.

7. The apparatus as defined in claim 6, wherein said bar code reader obtains identification of a subject sample rack, or of one or more sample containers held by said subject sample rack, or of sample contents contained in said containers held by said subject sample rack, prior to presenting said subject sample rack to an aspiration location of said automated analyzer for aspiration.

8. The apparatus as defined in claim 1, further comprising a presentation sensor for detection of motion errors or jams of said presentation moving mechanism.

9. The apparatus as defined in claim 1, further comprising an alignment mechanism for precise positioning of a sample rack presented for aspiration.

10. The apparatus as defined in claim 9, wherein said alignment mechanism comprises means for precise positioning of said presented sample rack along a lengthwise direction of said presented sample rack.

11. The apparatus as defined in claim 10, wherein said lengthwise direction precise positioning means comprises a spring-biased plunger engageable with said presented sample rack.

12. The apparatus as defined in claim 9, wherein said alignment mechanism further comprises means for precise positioning of said presented sample rack along a transverse direction of said presented sample rack.

13. The apparatus as defined in claim 12, wherein said transverse direction precise positioning means comprises a lead-in slot engageable with an engagement feature of said presented sample rack.

14. The apparatus as defined in claim 1, wherein said offload moving mechanism of said sample racks offload section comprises an offload pusher driven by an offload motor and capable of pushing either an individual one or a group of said sample racks.

15. The apparatus as defined in claim 1, further comprising an offload sensor for detection of motion errors or jams of said offload moving mechanism.

16. The apparatus as defined in claim 1, wherein said sample rack onload section, said sample rack presentation section, and said sample rack offload section are connected as one unit such that they can be moved together while maintaining their alignment.

17. The apparatus as defined in claim 1, further comprising electronic means coupled with said automated analyzer for integrated control and operation.

18. The apparatus as defined in claim 11, wherein said sample rack onload section, said sample rack presentation section and said sample rack offload section are connected as one unit such that they can be moved together while maintaining their alignment.

19. The apparatus as defined in claim 11, further comprising electronic means coupled with said automated analyzer for integrated control and operation.

20. Au apparatus for presenting sample racks to an automated analyzer, comprising:
   a. a sample rack onload section having an elongated rail having a distal end and a proximal end, and an onload moving mechanism movable along said rail for moving said sample racks placed on said rail towards said proximal end of said rail;
   b. an onload sensor located adjacent to said proximal end of said rail of said sample rack onload section for detection of motion errors or jams of said onload moving mechanism;
   c. a sample rack presentation section having a transfer area connected to said proximal end of said rail of said sample rack onload section for receiving said sample racks from said sample rack onload section, a sample presentation area adjacent to said automated analyzer for presenting sample racks for aspiration, and a presentation moving mechanism movable between said transfer area and said presentation area for moving at least one of said sample racks from said transfer area to said presentation area for sample aspiration and subsequently moving said at least one of said sample racks from said presentation area back to said transfer area after sample aspiration, wherein said transfer area can hold a plurality of said sample racks, wherein said plurality of sample racks can be presented simultaneously in said presentation area;
   d. a presentation sensor located at said presentation area of said sample rack presentation section for detection of motion errors or jams of said presentation moving mechanism;
   e. a sample rack offload section having an offload area connected to said transfer area of said sample rack presentation section for receiving said sample racks from said sample rack presentation section after a sample aspiration and an offload moving mechanism for moving said sample racks received from said sample rack presentation section to a sample rack offload tray; and
   f. an offload sensor located at said offload queue area of said sample rack offload section for detection of motion errors or jams of said offload moving mechanism.

21. The apparatus as defined in claim 20, wherein said onload moving mechanism of said sample racks onload section comprises an onload pusher capable of pushing either an individual one or a group of said sample racks.

22. The apparatus as defined in claim 20, wherein said onload moving mechanism of said sample racks onload section further comprises an onload motor for driving said onload pusher.

23. The apparatus as defined in claim 20, wherein said presentation moving mechanism of said sample racks presentation section further comprises means for simultaneously moving a multiplicity of said sample racks.

24. The apparatus as defined in claim 23, wherein said simultaneous moving means comprises a presentation tray driven by a presentation motor and capable of holding said multiplicity of said sample racks.

25. The apparatus as defined in claim 20, further comprising a bar code reader for obtaining the identification of said sample racks, or of one or more sample containers held by said sample racks, or of sample contents contained in said containers.

26. The apparatus as defined in claim 25, wherein said bar code reader obtains the identification of a subject sample rack, or of one or more sample containers held by said subject sample rack, or of sample contents contained in said containers held by said subject sample rack, prior to presenting said subject sample rack to an aspiration location of said automated analyzer for aspiration.

27. The apparatus as defined in claim 20, further comprising an alignment mechanism for the precise positioning of a sample rack presented for aspiration.

28. The apparatus as defined in claim 27, wherein said alignment mechanism comprises means for the precise positioning of said presented sample rack along a lengthwise direction of said presented sample rack.

29. The apparatus as defined in claim 28, wherein said lengthwise direction precise positioning means comprises a spring-biased plunger engageable with said presented sample rack.

30. The apparatus as defined in claim 27, wherein said alignment mechanism further comprises means for the precise positioning of said presented sample rack along a transverse direction of said presented sample rack.

31. The apparatus as defined in claim 30, wherein said transverse direction precise positioning means comprises a lead-in-slot engageable with an engagement feature of said presented sample rack.

32. The apparatus as defined in claim 20, wherein said offload moving mechanism of said sample racks offload section comprises an offload pusher driven by an offload motor and capable of pushing either an individual one or a group of said sample racks.

33. The apparatus as defined in claim 32, wherein said offload moving mechanism of said sample racks offload section comprises an offload pusher capable of pushing either an individual one or a group of said sample racks.

34. The apparatus as defined in claim 33, wherein said offload moving mechanism of said sample racks offload section further comprises an offload motor for driving said offload pusher.

35. An apparatus for presenting sample racks to an automated analyzer, comprising:
   a. a sample rack onload section having an elongated rail having a distal end and a proximal end, and an onload moving mechanism further comprising an onload pusher movable along said rail for moving said sample racks placed on said rail towards said proximal end of said rail;

b. an onload sensor located adjacent to said proximal end of said rail of said sample rack onload section for the detection of motion errors or jams of said onload moving mechanism;

c. a sample rack presentation section having a transfer area connected to said proximal end of said rail of said sample rack onload section for receiving said sample racks from said sample rack onload section, a sample presentation area adjacent to said automated analyzer for presenting sample racks for aspiration, and a presentation moving mechanism for moving at least one of said sample racks from said transfer area to said presentation area for a sample aspiration and subsequently moving said at least one of said sample racks from said presentation area back to said transfer area after sample aspiration, wherein said transfer area can hold a plurality of said sample racks, wherein said plurality of sample racks can be presented simultaneously in said presentation area;

d. a presentation sensor located at said presentation area of said sample rack presentation section for the detection of motion errors or jams of said presentation moving mechanism;

e. a sample rack offload section having an offload area connected to said transfer area of said sample rack presentation section for receiving said sample racks from said sample rack presentation section after a sample aspiration, and an offload moving mechanism further comprising an offload pusher for moving said sample racks received from said sample rack presentation section to a sample rack offload tray;

f. an offload sensor located at said offload queue area of said sample rack offload section for the detection of motion errors or jams of said offload moving mechanism; and g. a bar code reader for obtaining the identification of said sample racks, or of one or more sample containers held by said sample racks, or of sample contents contained in said containers.

36. The apparatus as defined in claim 35, wherein said onload moving mechanism of said sample racks onload section further comprises an onload motor for driving said onload pusher.

37. The apparatus as defined in claim 35, wherein said presentation moving mechanism of said sample racks presentation section further comprises the means for simultaneously moving a multiplicity of said sample racks.

38. The apparatus as defined in claim 37, wherein said simultaneous moving means comprises a presentation tray driven by a presentation motor and capable of holding said multiplicity of said sample racks.

39. The apparatus as defined in claim 35, wherein said bar code reader obtains the identification of a subject sample rack, or of one or more sample containers held by said subject sample rack, or of sample contents contained in said containers held by said subject sample rack, prior to presenting said subject sample rack to an aspiration location of said automated analyzer for aspiration.

40. The apparatus as defined in claim 35, further comprising an alignment mechanism for the precise positioning of a sample rack presented for aspiration.

41. The apparatus as defined in claim 40, wherein said alignment mechanism comprises the means for the precise positioning of said presented sample rack along a lengthwise direction of said presented sample rack.

42. The apparatus as defined in claim 41, wherein said lengthwise direction precise positioning means comprises a spring-biased plunger engageable with said presented sample rack.

43. The apparatus as defined in claim 40, wherein said alignment mechanism further comprises the means for the precise positioning of said presented sample rack along a transverse direction of said presented sample rack.

44. The apparatus as defined in claim 43, wherein said transverse direction precise positioning means comprises a lead-in slot engageable with an engagement feature of said presented sample rack.

45. The apparatus as defined in claim 35, wherein said offload moving mechanism of said sample racks offload section further comprises an offload motor for driving said offload pusher.

46. The apparatus as defined in claim 35, wherein said sample rack onload section, said sample rack presentation section and said sample rack offload section are connected as one unit such that they can be moved together while maintaining their alignment.

47. The apparatus as defined in claim 35, further comprising electronic means coupled with said automated analyzer for integrated control and operation.

* * * * *